United States Patent [19]

Shum et al.

[11] Patent Number: 5,475,042
[45] Date of Patent: Dec. 12, 1995

[54] CYCLIC PYROPHOSPHITES AND COMPOSITIONS STABILIZED THEREWITH

[75] Inventors: Sai P. Shum, Pleasantville, N.Y.; Stephen D. Pastor, Danbury, Conn.; Andrea R. Smith, Wingdale, N.Y.

[73] Assignee: Ciba-Geigy Corporation, Tarrytown, N.Y.

[21] Appl. No.: 407,742

[22] Filed: Mar. 21, 1995

[51] Int. Cl.$^6$ .................. C07F 9/6574; C08K 5/527
[52] U.S. Cl. .................................. 524/119; 558/78
[58] Field of Search .................. 558/78, 127, 128, 558/152; 524/119

[56] References Cited

U.S. PATENT DOCUMENTS

| | | |
|---|---|---|
| 2,691,010 | 10/1954 | Anderson ................................. 554/78 |
| 2,722,539 | 11/1955 | Anderson ................................. 554/78 |
| 4,143,028 | 3/1979 | Spivack . |
| 4,318,845 | 3/1982 | Spivack et al. . |
| 4,374,219 | 2/1983 | Spivack et al. . |
| 4,481,317 | 11/1984 | Nakahara et al. . |
| 4,524,166 | 6/1985 | Spivack et al. . |
| 4,912,155 | 3/1990 | Burton . |
| 4,999,393 | 3/1991 | Haruna et al. . |
| 5,292,785 | 3/1994 | Pastor et al. . |

FOREIGN PATENT DOCUMENTS 462902 3/1971 Japan .

OTHER PUBLICATIONS

Index Chemicus, vol. 28, #1, Jan. 2, 1968, abstract No. 89519.
Helvetica Chimica Acta vol. 76 (1993).
Phosphorus and Sulfur, 1984, vol. 19 pp. 285–293.
Phosphorus and Sulfur, 1984, vol. 19 pp. 1–10.
Phosphorus and Sulfur, 1983, vol. 15, pp. 253–256.
J. Heterocyclic Chem., 20, 1311 (1983).
Phosphorus and Sulfur, 1983, vol. 15, pp. 9–13.
J. P. Spivack, et al., Polymer Stabilization and Degradation, P. P. Klemchuk pp. 247–257.

*Primary Examiner*—Veronica P. Hoke
*Attorney, Agent, or Firm*—Luther A. R. Hall

[57] ABSTRACT

Novel cyclic pyrophosphite of formula I

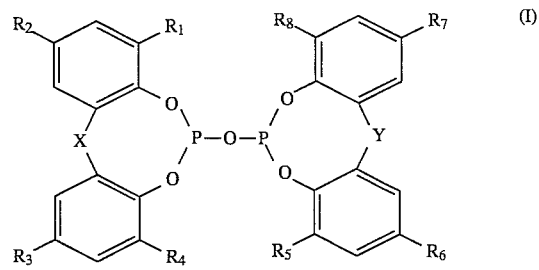

are prepared from the corresponding 6-chloro and 6-oxo phosphepins or phosphocins. The cyclic pyrophosphites are effective process stabilizers for organic materials subject to thermal, oxidative or actinic induced degradation, particularly polyolefins and especially polypropylene.

17 Claims, No Drawings

CYCLIC PYROPHOSPHITES AND COMPOSITIONS STABILIZED THEREWITH

The instant invention pertains to novel cyclic pyrophosphites and to compositions stabilized therewith.

BACKGROUND OF THE INVENTION

The use of organic trivalent phosphorus compounds, such as organic phosphites and phosphonites, for the stabilization of polymeric substrates subject to thermal, oxidative and/or actinic light induced degradation is known. U.S. Pat. Nos. 4,143,028; 4,318,845; 4,374,219; 4,524,166; 4,912,155 and 4,999,393 describe the use of seven- and eight-membered dibenzo[d,f][1,3,2]dioxaphosphepins and dibenzo[d,g][1,3,2]dioxaphosphocins as effective stabilizers for organic materials.

J. D. Spivack et al., Polymer Stabilization and Degradation, P. P. Klemchuk, editor, American Chemical Society, Washington, D.C., 1985, 247–257, describe the use of hydrolytically-stable seven- and eight-membered dibenzo[d,f][1,3,2]dioxaphosphepins and dibenzo[d,g][1,3,2]dioxaphosphocins, respectively, as processing stabilizers. The detailed synthesis, spectroscopic data and structural conformation of seven- and eight-membered dibenzo[d,f][1,3,2]dioxaphosphepins and dibenzo[d,g][1,3,2]dioxaphosphocins are described by S. D. Pastor et al. in Phosphorus and Sulfur, 15, 9 and 253 (1983); J. Heterocyclic Chem., 20, 1311 (1983); Phosphorus and Sulfur, 19, 1 and 285 (1984), Helv. Chim. Acta, 76, 900 (1993) and U.S. Pat. No. 5,292, 785.

U.S. Pat. No. 4,481,317 discloses the synthesis of higher molecular weight hindered bisphenol diphosphonites and their use as stabilizers for polyolefins for protection against ultraviolet light and as protection for the high temperature processing of the polymer.

Japanese Sho 46/2902 reports that low molecular weight acyclic pyrophosphites are known and are useful as process stabilizers for PVC and PVC/ABS copolymers. Neither the cyclic pyrophosphites nor their use as stabilizers for organic materials subject to oxidative, thermal or actinic light induced degradation is described or suggested by the prior art.

OBJECTS OF THE INVENTION

One object of this invention is to provide new cyclic pyrophosphites.

Another object is to provide organic compositions stabilized against thermal, oxidative and/or actinic light induced degradation by the presence of said new cyclic pyrophosphites either alone or in combination with a hindered phenolic antioxidant, a hindered amine thermal stabilizer, a hydroxylamine, a benzofuran-2-one or mixture thereof.

DETAILED DISCLOSURE

The instant invention pertains to new cyclic pyrophosphites of formula I

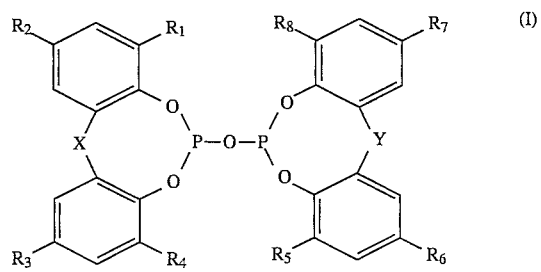

wherein $R_1$, $R_2$, $R_3$, $R_4$, $R_5$, $R_6$, $R_7$ and $R_8$ are independently hydrogen, alkyl of 1 to 18 carbon atoms, cycloalkyl of 5 to 12 carbon atoms or phenylalkyl of 7 to 15 carbon atoms, and X and Y are independently a direct bond, —S— or —$CR_9R_{10}$— where $R_9$ and $R_{10}$ are independently hydrogen or alkyl of 1 to 18 carbon atoms, or $R_{10}$ is also phenyl.

Preferably, $R_1$, $R_2$, $R_3$, $R_4$, $R_5$, $R_6$, $R_7$ and $R_8$ are independently alkyl of 1 to 18 carbon atoms, and most preferably alkyl of 1 to 8 carbon atoms, most especially methyl or tert-butyl.

Preferably, X and Y are independently a direct bond or —$CR_9R_{10}$— where $R_9$ is hydrogen, and $R_{10}$ is hydrogen, methyl or phenyl.

When any of $R_1$ to $R_{10}$, is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl and n-octadecyl; when cycloalkyl, they are, for example, cyclopentyl, cyclohexyl, 1-methylcyclohexyl, cyclooctyl and cyclododecyl; or when phenylalkyl, they are, for example, benzyl, 1-phenylethyl, 2-phenylethyl and α, α-dimethylbenzyl; so that —$CR_9R_{10}$ is, for example, methylene, ethylidene, 2,2-isopropylidene, 1,1-butylidene, 1,1-octylidene and benzylidene.

The instant invention also pertains to a composition stabilized against thermal, oxidative or light-induced degradation which comprises, (a) an organic material subject to thermal, oxidative or light-induced degradation, and (b) an effective stabilizing amount of a compound of formula I.

Preferably, the organic material is a natural, semi-synthetic or synthetic polymer, especially a thermoplastic polymer.

Most preferably, the polymer is a polyolefin, especially polyethylene or polypropylene; most especially polypropylene.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE). Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, mine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene,/isoprene/styrene,/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
 1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)

4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)
1,1-bis-(5-tert-butyl-4-hydroxy-2-methylphenyl )-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)- 6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β(5-tert-butyl-4hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-,5'-(1,1,3,3-tetramethylbutyl)-,5-chloro-3',5'-di-tert-butyl-,5-chloro-3'-tert-butyl-5'-methyl-, 3'-sec-butyl-5'-tert-butyl-, 4'-octoxy,3', 5'-di-tert-amyl-, 3',5'-bis-(α, α-dimethylbenzyl),3'-tert-butyl-5'-(2-(omega-hydroxy-octa-(ethyleneoxy)carbonyl-ethyl)-,3'-dodecyl-5'-methyl-, and 3'-tert-butyl-5'-(2-octyloxycarbonyl)ethyl-, and dodecylated- 5'-methyl derivatives.

2.2. 2-Hydroxy-benzophenones, for example, the 4-hydroxy-,4-methoxy-,4-octoxy,4-decyloxy-,4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β, β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert-butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide,2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy- 4-oxtyloxyphenyl)-s-triazine;2,6-bis-(2,4-dimethylphenyl)-4-(2,4-dihydroxyphenyl)-s-triazine; 2,4-bis(2,4-dihydroxyphenyl)-6-(4- chlorophenyl)-s-triazine; 2,4-bis[2-hydroxy-4-(2-hydroxyethoxy)phenyl]-6-(4-chlorophenyl)-s-triazine;2,4-bis[2-hydroxy-4-(2-hydroxy-4-(2-hydroxyethoxy)phenyl]-6-(2,4-dimethylphenyl)-s-triazine;2,4-bis[2-hydroxy-4-(2-hydroxyethoxy) phenyl]-6-(4-bromophenyl)-s-triazine;2,4-bis[2-hydroxy-4-(2-acetoxyethoxy)phenyl]-6-(4-chlorophenyl)-s-triazine,2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine,3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecyl nitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, 3-[ 4-(2-acetoxyethoxy)phenyl]-5,7-di-tert-butyl-benzofuran-2-one,5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one],5,7-di-tert-butyl-3-(4-ethoxyphenyl)benzofuran-2-one,3(4-acetoxy-3,5-dimethylphenyl)-5,7-di-tert-butyl-benzofuran-2-one,3-(3,5-di-methyl- 4-pivaloyloxyphenyl)-5,7-di-tert-butyl-benzofuran-2-one.

The co-stabilizers, with the exception of the benzofuranones listed under 11, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. No. 4,325,863, U.S. Pat. No. 4,338 244 or U.S. Pat. No. 5,175,312.

Examples of such benzofuran-2-ones are compounds of the formula

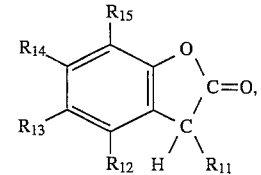

in which $R_{11}$ is phenyl or phenyl which is substituted by 1 to 3 alkyl radicals together having at most 18 carbon atoms, alkoxy having 1 to 12 carbon atoms, alkoxycarbonyl having 2 to 18 carbon atoms or chlorine;

$R_{12}$ is hydrogen;

$R_{14}$ is hydrogen, alkyl having 1 to 12 carbon atoms, cyclopentyl, cyclohexyl or chlorine;

$R_{13}$ has the meaning of $R_{12}$ or $R_{14}$ is a radical of the formula

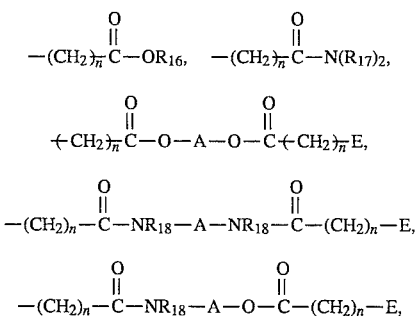

-continued

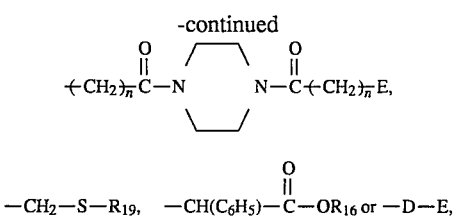

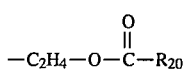

in which
R$_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals together having at most 18 carbon atoms;
n is 0, 1 or 2;
the substituents R$_{17}$, independently of one another, are hydrogen, alkyl having 1 to 18 carbon atoms, cyclopentyl, cyclohexyl, phenyl, phenyl which is substituted by 1 or 2 alkyl radicals together having at most 16 carbon atoms, a radical of the formula —C$_2$H$_4$OH, —C$_2$H$_4$—O—C$_m$H$_{2\,m+1}$ or $$-C_2H_4-O-\overset{O}{\underset{\|}{C}}-R_{20}$$

together with the nitrogen atom to which they are attached form a piperidine or morpholine radical;
m is 1 to 18;
R$_{20}$ is hydrogen, alkyl having 1 to 22 carbon atoms or cycloalkyl having 5 to 12 carbon atoms;
A is alkylene having 2 to 22 carbon atoms which may be interrupted by nitrogen, oxygen or sulfur;
R$_{18}$ is hydrogen, alkyl having 1 to 18 carbon atoms, cyclopentyl, cyclohexyl, phenyl, phenyl which is substituted by 1 or 2 alkyl radicals together having at most 16 carbon atoms, or is benzyl;
R$_{19}$ is alkyl having 1 to 18 carbon atoms;
D is —O—, —S—, —SO—, —SO$_2$— or —C(R$_{21}$)$_2$—;
the substituents R$_{21}$, independently of one another, are hydrogen, C$_1$–C$_{16}$ alkyl, the two R$_{21}$ together containing 1 to 16 carbon atoms, R$_{21}$ is furthermore phenyl or a radical of the formula

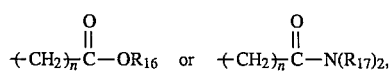

in which n, R$_{16}$ and R$_{17}$ are as defined above;
E is a radical of the formula

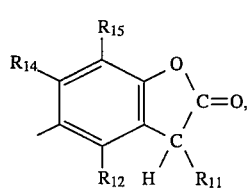

in which R$_{11}$, R$_{12}$ and R$_{14}$ are as defined above; and R$_{15}$ is hydrogen, alkyl having 1 to 20 carbon atoms, cyclopentyl, cyclohexyl, chlorine, or a radical of the formula

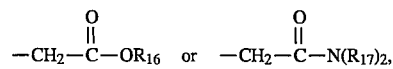

in which R$_{16}$ and R$_{17}$ are as defined above, or R$_{15}$ together with R$_{14}$ forms a tetramethylene radical.

Preference is given to those benzofuran-2-ones in which R$_{13}$ is hydrogen, alkyl having 1 to 12 carbon atoms, cyclopentyl, cyclohexyl, chlorine or a radical of the formula

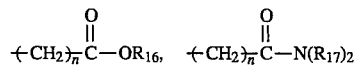

or —D—E, in which n, R$_{16}$, R$_{17}$, D and E are as defined above, R$_{16}$ is in particular hydrogen, alkyl having 1 to 18 carbon atoms, cyclopentyl or cyclohexyl.

Preference is given furthermore to those benzofuran-2-ones in which R$_{11}$ is phenyl or phenyl which is substituted by 1 or 2 alkyl radicals together having at most 12 carbon atoms; R$_{12}$ is hydrogen; R$_{14}$ is hydrogen or alkyl having 1 to 12 carbon atoms; R$_{13}$ is hydrogen, alkyl having 1 to 12 carbon atoms,

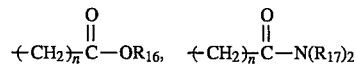

or —D—E; R$_{15}$ is hydrogen, alkyl having 1 to 20 carbon atoms,

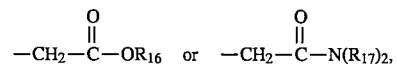

R$_{15}$ together with R$_{14}$ forms a tetramethylene radical, n, R$_{16}$, R$_{17}$, D and E being as defined at the beginning.

Of particular interest are also those benzofuran-2-ones in which R$_{11}$ is phenyl; R$_{13}$ is hydrogen, alkyl having 1 to 12 carbon atoms or —D—E; R$_{12}$ and R$_{14}$, independently of one another, are hydrogen or alkyl having 1 to 4 carbon atoms; and R$_{15}$ is alkyl having 1 to 20 carbon atoms, D and E being as defined at the beginning.

Of special interest are finally also those benzofuran-2-ones in which R$_{11}$ is phenyl; R$_{13}$ is alkyl having 1 to 4 carbon atoms or —D—E; R$_{12}$ and R$_{14}$ are hydrogen; and R$_{15}$ is alkyl having 1 to 4 carbon atoms, cyclopentyl or cyclohexyl, D being a group —C(R$_{21}$)$_2$— and E being a radical of the formula

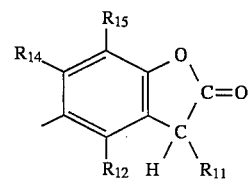

the substituents R$_{21}$ being identical to or different from one another and each being alkyl having 1 to 4 carbon atoms, and R$_{11}$, R$_{12}$, R$_{14}$ and R$_{15}$ being as defined.

The amount of additional additives, in particular stabilizers, for example of the benzofuran2-ones mentioned, can vary within wide limits. For example, 0.0005 to 10, preferably 0.00 1 to 5, in particular 0.01 to 2,% by weight thereof can be present in the compositions according to the invention.

Incorporation of the instant compound of formula I and, if desired, further additives in the polymer organic material is carried out by known methods, for example before or during moulding or by applying the dissolved or dispersed compounds to the polymer organic material, if appropriate with subsequent slow evaporation of the solvent. The beta, triclinic modification according to the invention can also be added to the materials to be stabilized in the form of a masterbatch containing them, for example, in a concentration of 2.5 to 25% by weight.

The instant compound of formula I according to the invention can also be added before or during polymerization or before crosslinking.

The instant compound of formula I according to the invention can be incorporated in the material to be stabilized in pure form or encapsulated in waxes, oils or polymers.

The instant compound of formula I according to the invention can also be sprayed onto the polymer to be stabilized. They are capable of diluting other additives (for example the abovementioned customary additives) or their melts, thus enabling them to be sprayed onto the polymer to be stabilized also together with these additives. Addition by spraying during deactivation of the polymerization catalysts is particularly advantageous, it being possible, for example, for the steam used for deactivation to be used for spraying.

In the case of bead polymerized polyolefins, it may be advantageous, for example, to apply the instant compound of formula I according to the invention, if desired together with other additives, by spraying.

The materials thus stabilized can be used in a wide range of forms, for example as films, fibres, tapes, moulding compositions, profiles or as binders for paints, adhesives or cements.

As already mentioned, the organic materials to be protected are preferably organic, in particular synthetic, polymers. Of these, the materials being protected are particularly advantageously thermoplastic materials, in particular polyolefins. The excellent efficiency of the alkanolamine esters of acyclic phosphites of formula I as processing stabilizers (thermal stabilizers) should be mentioned in particular. To this end, it is advantageously added to the polymer before or during its processing. It is however also possible to stabilize other polymers (for example elastomers) or lubricants or hydraulic fluids against degradation, for example light-induced or thermal-oxidative degradation. For elastomers, see the above list of possible organic materials.

Suitable lubricants and hydraulic fluids are based, for example, on mineral or synthetic oils or mixtures thereof. Lubricants are known to one skilled in the art and described in the relevant technical literature, for example in Dieter Klamann, "Schmierstoffe und verwandte Produkte" (Verlag Chemie, Weinheim 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie" vol. 13, pages 85–94 (Verlag Chemie, Weinheim, 1977).

Accordingly, a preferred embodiment of the present invention is the process of using the instant compound of formula I for stabilizing organic materials against oxidative, thermal or light-induced degradation.

The instant compound according to the invention is preferably used as processing stabilizer (thermal stabilizer) of thermoplastic polymers.

The present invention also provides a process for stabilizing an organic material against oxidative, thermal or light-induced degradation, which comprises incorporating therein or applying thereto an instant compound of formula I.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate. 1,3,5-tris(3, 5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-( 3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis( 3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis [2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl- 4-hydroxybenzyl)isocyanurate,2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), poly-condensation product of 1-(2-hydroxyethyl)-2,2,6,6-tetramethyl-4-hydroxypiperidine and succinic acid, polycondensation product of 4,4'-hexamethylenebis-(amino-2,2, 6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylene-bis(amino-2,2,6,6-tetramethylpiperidine), N,N',N",N"'-tetrakis[(4,6-bis(butyl-2,2,6,6-tetra-methyl-piperidin-4-yl)-amino-s-triazin-2-yl]-1,10-diamino-4,7-diazadecane, mixed [2,2,6,6-tetra-methyl-piperidin-4-yl/β,β,β', β'-tetramethyl-3,9-(2,4,8,10-tetraoxaspiro[5.5]-undecane) diethyl]1,2,3,4-butanetetracarboxylate, mixed [1,2,2,6,6-pentamethylpiperidin-4-yl/β,β,β',β'-tetramethyl-3,9-(2,4,8, 10-tetraoxaspiro[5.5]-undecane)diethyl]1,2,3,4-butanetetra-carboxylate, octamethylene bis(2,2,6,6-tetramethyl-piperidin-4-carboxylate), 4,4'-ethylenebis(2,2,6,6-tetramethylpiperazin-3-one), and bis(1-octyloxy-2,2,6,6-tetramethyl-piperidin- 4-yl)sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl(2,2,6,6-tetramethyl-piperidin-4-yl)amino)-s-triazine-2-yl]-1,10-di-amino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent brightstocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$—OCC-alkylene—COO$G_2$ wherein "alkylene" denotes an alkylene residue having from 2 to 14 carbon atoms and $G_1$ $G_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants 1. Alkylated Monophenols 2,6-Di-tert-butyl-4-methylphenol, 2,6-di-tert-butylphenol, 2-tert-butyl-4,6-dimethylphenol,2,6-di-tert-butyl-4-ethyl-phenol, 2,6-di-tert-butyl-4-n-butylphenol, 2,6-di-tert-butyl-4-di-butylphenol, 2,6-di-cyclopentyl-4-methylphenol, 2-(β-methylcyclohexyl)-4,6-dimethylphenol, 2,6-di-octa-decyl-4-methylphenol, 2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or-5-isobutylphenol), 2,2'-methylene-bis-( 6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl- 2-hydroxybenzyl)-4-methyl-phenol, 1,1,3-tris-( 5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)butyrate], bis-(3-tert-butyl-4-hydroxy-5-methylphenyl)-dicyclopentadiene, bis-[2-(3'-tert-butyl-2'-hydroxy-5'-methyl- benzyl)- 6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3, 5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols 4-Hydroxy-lauric acid anilide, 4-hydroxy-stearic acid anilide, 2,4-bis-octylmercapto-6-(3, 5-di-tert-butyl-4-hydroxyanilino)-s-triazine, N-(3,5-di-tert-butyl-4-hydroxyphenyl )-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexammethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants:
N,N'-Di-isopropyl-p-phenylenediamine, N,N'-di-sec.-butyl-p-phenylenediamine, N,N'-bis(1,4-di-methyl-pentyl)-p-phenylenediamine, N,N'-bis(1-ethyl-3-methyl-pentyl)-p-phenylenediamine, N,N'-bis( 1-methyl-heptyl)-p-phenylenediamine, N,N'-dicyclo-hexyl-p-phenylenediamine, N,N'-diphenyl-p-phenylenediamine, N,N'-di-(naphthyl-2-)-p-phenylenediamine, N-iso-propyl- N'-phenyl-p-phenylenediamine, N-(1,3-dimethyl-butyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-di-methyl,N,N'-di-sec-butyl-p-phenylenediamine, di-phenylamine, N-allyldiphenylamine, 4-iso-propoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyryl-amino-phenol, 4-nonanoylamino-phenol, 4-dodecanoyl-amino-phenol, 4-octa-decanoyl-amino-phenol, di-(4-methoxy-phenyl)-amine, 2,6-di-tert-butyl-4-dimethyl-amino-methyl-phenyl,2,4'-diamino-diphenylmethane, 4,4'-diamino-diphenyl-methane, N,N,N',N'-tetramethyl-4,4'-di-amino-diphenylmethane, 1,2-di-(phenyl-amino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-di-methyl-4H-1,4-benzothiazine, phenothiazine, N-allylphenothiazine, tert-octylated phenothiazine, 3,7-di-tert-octylphenothiazine.

Examples for other antioxidants:

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

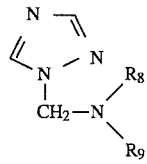

which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-monooleate, lead-naphthenate, alkenyl-succinic acids and-anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonyl-naphthalene-n-sulfonates, calcium petroleum sulfonates.

e) Derivatives of gamma-alkoxypropylamines described in Japanese Patent Publication No. 5783/1973; and f) Salts having the formula $Y-NH_3-R_{10}CO_2-$ in which Y is a group $R_{11}X_1 CH_2CH(OH)CH_2$ in which $R_{10}$ and $R_{11}$, independently, are e.g. alkyl and $X_1$ is O, $CO_2$, NH, N(alkenyl) or S, these salts being prepared by mixing an amine $Y-NH_2$ with an acid $R_{10}CO_2H$, as disclosed in DE-OS 3437 876 (German Offenlegungsschift).

g) Compounds having the formula

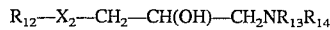

in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$ alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

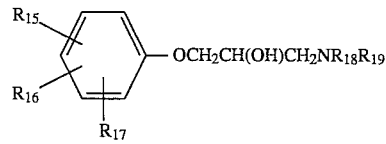

in which $R_{15}$, $R_{16}$, $R_{17}$ are, independently, hydrogen, $C_1-C_{15}$alkyl,$C_5-C_{12}$cycloalkyl, $C_6-C_{15}$aryl or $C_7-C_{12}$aralkyl and $R_{18}$ $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are:

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are:

Polymethacrylates, alkylated naphthalene derivatives.

Examples of dispersants/detergents are:

Polybutenylsuccinic acid-amides or-imides, polybutenyl-phosphonic acid derivatives, basic magnesium-, calcium-, and bariumsulfonates and -phenolates.

Examples of anti-wear additives and extreme pressure additives are:

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are for the purpose illustration only and are not to be construed to limit the scope of the instant invention in any manner whatsoever.

EXAMPLE 1

6-Chloro-2,4,8,10-tetra-tert-butyl-dibenzo[d,f][1,3,2]dioxaphosphepin

To a solution of 55.2 g (130 mmol) of 2,2'-bis(4,6-di-tert-butylphenol) and 1.82 mL (19 mmol) of 1-methyl-2-pyrrolidinone in 400 mL of toluene at ambient temperature is added dropwise 16.6 mL (19 mmol) of phosphorus trichloride. After the addition is complete, the reaction mixture is heated at reflux for 18 hours. After cooling to ambient temperature, the toluene is removed in vacuo from the reaction mass. The reaction mass is then recrystallized from 300 mL of acetonitrile. The recrystallization solvent is decanted from the reaction residue which is then dried under vacuum to give 39.9 g (64.5%) yield of an off-white solid as the title compound melting at 183°–186° C.

Analysis: Calcd for $C_{28}H_{40}ClO_2P$: C, 70.8;H,8.4. Found: C,70.6;H,8.5.

EXAMPLE 2

6-Oxo-2,4,8,10-tetra-tert-butyl-dibenzo[d,f][1,3,2]dioxaphosphepin

To a solution of 6.32 g (13 mmol) of the compound of Example 1 in 150 mL of toluene at ambient temperature is added dropwise a solution of 0.24 mL (13 mmol) of distilled water in 3.0 mL (22 mmol) of triethylamine. After the addition is complete, the reaction mixture is stirred at ambient temperature for 15 minutes. The reaction solvent is removed in vacue and the reaction mass is then recrystallized twice with 50 mL of acetonitrile. The recrystallization solvent is removed under vacuum and the residue is dried under vacuum to afford the title compound in a yield of 5.2 g (86.3%) as an off-white solid melting at 218° C.

Analysis: Calcd for $C_{28}H_{41}O_3P$: C,73.6;H,9.1; Found: C,73.2;H,9.7.

EXAMPLE 3

6-{[2,4,8,10-Tetra-tert-butyl-dibenzo[d,f][1,3,2]dioxaphosphepin-6-yl]oxy}-2,4,8,10-tetra-tert-butyl-dibenzo[d,f][1,3,2]dioxaphosphepin To a suspension of 0.18 g (7.5 mmol) of sodium hydride in 50 mL of dry tetrahydrofuran is added dropwise a solution of 3.56 g (7.8 mmol) of the compound of Example 2 in 80 mL of dry tetrahydrofuran. After addition is complete, the reaction mixture is heated to 60° C. for 9.5 hours. The reaction mixture is then cooled to about 0° C. To the reaction mixture is added 3.67 g (7.7 mmol) of the compound of Example 1 at 3° C. The reaction mixture is stirred for 14 hours at ambient temperature. The reaction solvent is removed under vacuum and the residue is a crude product which is purified by chromatography (hexane:ethyl acetate; 95:5). The purified product is then re, crystallized once from acetonitrile and then from 2-butanone to yield the title compound as a white solid melting at 269° C.

Analysis: Calcd for $C_{56}H_{80}O_5P_2$: C,75.1;H,9.0. Found: C, 74.8;H,9.1.

EXAMPLE 4

6-Chloro-2,4,8,10-tetra-tert-butyl-12H-dibenzo[d,g][1,3,2]dioxaphosphocin

To a solution of 25.0 g (0.059 mol) of 2,2'-methylenebis(4,6-di-tert-butylphenol) and 0.57 mL (5.9 mmol) of 1-methyl-2-pyrrolidinone in 275 mL of toluene at ambient temperature is added dropwise 5.16 mL (0.059 mol) of phosphorus trichloride. After the addition is complete, the reaction mixture is refluxed for eight hours. After cooling the mixture to ambient temperature, the toluene is removed in vacuo and the reaction mass is re, crystallized twice from 250 mL of 98% acetonitrile and 2% toluene (% by volume) in acetonitrile. The recrystallization solvent is removed by decantation and the residue is dried under vacuum to give 21.4 g (79% yield) of the title compound as an off-white solid melting at 227°–230° C.

Analysis: Calcd for $C_{29}H_{42}ClO_2P$: C,71.2;H,8.7. Found: C, 71.1;H,8.9.

EXAMPLE 5

6-Oxo-2,4,8,10-tetra-tert-butyl-12H-dibenzo[d,g][1,3,2]dioxaphosphocin

To a solution of 8.9 g (0.019 mol) of the compound of Example 4 in 150 mL of toluene at ambient temperature is added dropwise a solution of 0.34 mL (0.019 mol) of distilled water in 4.0 mL (0.029 mol) of triethylamine. After the addition is complete, the reaction mixture is stirred at ambient temperature for 15 minutes. The reaction solvent is removed under vacuum and the residue is recrystallized twice with 50 mL of acetonitrile. The acetonitrile is then removed in vacuo and the residue is dried under vacuum to give 2.4 g (79.5% yield) of the title compound as an off-white solid melting at 164° C.

Analysis: Calcd for $C_{29}H_{43}O_3P$: C,74.0;H,9.2. Found: C, 73.3;H,9.8.

EXAMPLE 6

6-{[2,4,8,10-Tetra-tert-butyl-12H-dibenzo[d,g][1,3,2]dioxaphosphocin-6-yl]oxy}-2,4,8,10-tetra-tert-butyl-12H-dibenzo[d,g][1,3,2]dioxaphosphocin To a solution of 2.0 g (4.3 mmol) of the compound of Example 5 in 150 mL of toluene is added 2.1 g (4.3 mmol) of the compound of Example 4 and 3.0 mL (22 mmol) of triethylamine at ambient temperature. The reaction mixture is stirred at room temperature for 14 hours. The solvent is removed under vacuum and the residue is recrystallized twice from acetonitrile to give the title compound as a white solid melting at 249°–252° C.

Analysis: Calcd for $C_{58}H_{84}O_5P_2$: C,75.4;H9.2. Found: C, 75.1;H,9.5.

EXAMPLE 7

6-Chloro-2,4,8,10-tetra-tert-butyl-12-methyl-dibenzo[d,g][1,3,2]dioxaphosphocin To a solution of 50.9 g. (0.12 mol) of 2,2'-ethylidenebis(4,6-di-tert-butylphenol) and 1.73 mL (0.018 mol) of 1-methyl-2-pyrrolidinone in 275 mL of toluene at ambient temperature is added dropwise 15.7 mL (0.18 mol) of phosphorus trichloride. After the addition is complete, the reaction mixture is heated at reflux for 18 hours. After cooling to room temperature, the toluene is removed in vacuo and the residue is then recrystallized twice from 250 mL of acetonitrile. The acetonitrile is decanted from the product which is dried under vacuum to give 21.0 g (34.8% yield) of the title compound as an off-white solid melting at 194°–198° C.

Analysis: Calcd for $C_{30}H_{44}ClO_2P$: C,71.6;H,8.8. Found: C, 71.6;H,9.1.

EXAMPLE 8

6-Oxo-2,4,8,10-tetra-tert-butyl-12-methyl-
dibenzo[d,g][1,3,2]dioxaphosphocin

To a solution of 5.5 g (11 mmol) of the compound of Example 7 in 100 mL of toluene at ambient temperature is added dropwise a solution of 0.20 mL (11 mmol) of distilled water in 3.0 mL (22 mmol) of triethylamine. After the addition is complete, the reaction mixture is stirred at room temperature for 15 minutes. The toluene is removed under vacuum and the residue is recrystallized twice from 50 mL of diethyl ether. The ether is removed in vacuo and the residue is dried under vacuum to give 3.95 g (74% yield) of the title compound as an off-white solid melting at 209° C.

Analysis: Calcd for $C_{30}H_{45}O_3P$: C,74.3;H,9.4. Found: C, 74.0;H,9.9.

EXAMPLE 9

6-{[2,4,8,10-Tetra-tert-butyl-12-methyl-
dibenzo[d,g][1,3,2]dioxaphosphocin-6-yl]oxy}-
2,4,8,10-tetra-tert-butyl-12-methyl-
dibenzo[d,g][1,3,2]dioxaphosphocin To a solution of 17.3 g (36 mmol) of the compound of Example 8 in 250 mL of dry tetrahydrofuran (THF) is added 1.0 g (41 mmol) of sodium hydride at 3° C. After the addition is complete, the reaction mixture is allowed to warm to room temperature. The reaction mixture is then stirred for 14 hours at ambient temperature. To the reaction mixture is then added 14.8 g(29 mmol) of the compound of Example 7 at ambient temperature. After 48 hours, the reaction mixture is filtered and the filtrate is concentrated under vacuum. The residue is purified by flash chromatography with 1% ethyl acetate/99% hexane to give the title compound as a white solid melting at 281°–285° C.

Analysis: Calcd for $C_{60}H_{88}O_5P_2$: C,75.7;H,9.3. Found: C, 75.3;H,9.7.

EXAMPLE 10

6-{[2,4,8,10-Tetra-tert-butyl-12-methyl-
dibenzo[d,g][1,3,2]dioxaphosphocin-6-yl]oxy}-
2,4,8,10-tetra-tert-butyl-12-methyl-
dibenzo[d,g][1,3,2]dioxaphosphocin To a solution of 5.44 g (11 mmol) of the compound of Example 8 in 120 mL of toluene and 1.7 mL (13 mmol) of triethylamine is added 5.53 g (11 mmol) of the compound of Example 7 at ambient temperature. The reaction mixture is stirred at room temperature for 7 days. The toluene is then removed under vacuum and the residue is recrystallized from acetonitrile. The recrystallized product is then recrystallized a second time from 98% acetonitrile/2% toluene; and finally a third time from hexane to give the title compound as a white solid melting at 302°–305° C.

Analysis: Calcd for $C_{60}H_{88}O_5P_2$: C,75.7;H,9.3. Found: C, 75.2;H,9.5.

EXAMPLE 11

6-{[2,4,8,10-Tetra-tert-butyl-
dibenzo[d,f][1,3,2]dioxaphosphepin-6-yl]oxy}-
2,4,8,10-tetra-tert-butyl
-12H-dibenzo[d,g][1,3,2]dioxaphosphocin To a solution of 3.06 g (6.5 mmol) of the compound of Example 5 in 125 mL of toluene is added 3.09 g (6.5 mmol) of the compound of Example 1 and 1.8 mL (13 mmol) of triethylamine. The reaction mixture is stirred at room temperature for 4.5 hours. The toluene is removed under vacuum and the residue is recrystallized from 98% acetonitrile/2% toluene. The product isolated is a mixture containing the title compound as one component as identified by $^{31}P$ nmr.

EXAMPLE 12

Process Stabilization of Polypropylene at 525° F. (274° C.)

The base formulation comprises unstabilized, high yield/high selectivity Spheripol polypropylene (PROFAX® 6501, Himont) containing 0.075% by weight of calcium stearate. The test additives are incorporated into the polyproylene by dry blending using a minimum amount of methylene chloride solvent. The solvent is then removed by evaporation under reduced pressure. The stabilized resin formulation is extruded at 90 rpm from a 1 inch (2.54 cm) diameter extruder (screw to wall clearance adjusted tighter than normal for harsher than normal processing conditions) at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive | Concentration (% by weight) | Melt Flow after Extrusion | |
| --- | --- | --- | --- |
| | | 1 | 5 |
| None | — | 12.4 | 55.7 |
| Compound of Example 3 | 0.075 | 6.8 | 15.3 |

These results show that the stabilized composition of the instant invention provides greatly improved melt flow stabilization to polypropylene.

Similar results are observed when the compound of Example 9 is used to stabilize polypropylene in place of the compound of Example 3.

EXAMPLE 13

Process Stabilization of Polypropylene at 525° F. (274° C.)

Following the procedure of Example 12, polypropylene containing a phenolic antioxidant in combination with an instant compound is extruded and the melt flow rate (in grams/10 minutes) determined by ASTM method D1238 on the pellets obtained from the extruder after each of the first and fifth extrusions. The results are given in the table below.

| Additive* | Concent. (% by wt) | Melt Flow Values after Extrusion | |
| --- | --- | --- | --- |
| | | 1 | 5 |
| None | — | 12.4 | 55.7 |
| AO A | 0.075 | 8.3 | 13.9 |
| AO A plus Example 3 Compound | 0.075 0.075 | 5.6 | 8.3 |

| | Concent. | Melt Flow Values after Extrusion | |
|---|---|---|---|
| Additive* | (% by wt) | 1 | 5 |

*AO A is neopentanetetrayl tetrakis(3,5-di-tert-butyl-4-hydroxyhydrocinnamate).

The combination of a phenolic antioxidant plus an instant compound provides excellent melt flow stabilization; better stabilization than obtained by the use of a phenolic antioxidant alone.

Similar results are observed when the compound of Example 9 is used in place of the compound of Example 3 in conjunction with a phenolic antioxidant to stabilize polypropylene.

What is claimed is:

1. A cyclic pyrophosphites of formula I

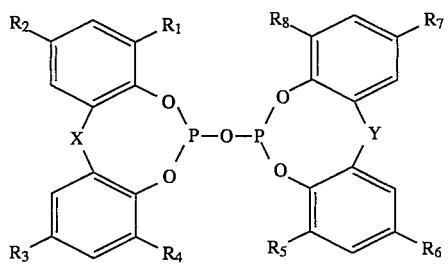

wherein $R_1$, $R_2$, $R_3$, $R_4$, $R_5$, $R_6$, $R_7$ and $R_8$ are independently hydrogen, alkyl of 1 to 18 carbon atoms, cycloalkyl of 5 to 12 carbon atoms or phenylalkyl of 7 to 15 carbon atoms, and X and Y are independently a direct bond, —S— or —$CR_9R_{10}$— where $R_9$ and $R_{10}$ are independently hydrogen or alkyl of 1 to 18 carbon atoms, or $R_{10}$ is also phenyl.

2. A compound according to claim 1 wherein $R_1$, $R_2$, $R_3$, $R_4$, $R_5$, $R_6$, $R_7$ and $R_8$ are independently alkyl of 1 to 18 carbon atoms.

3. A compound according to claim 2 wherein $R_1$, $R_2$, $R_3$, $R_4$, $R_5$, $R_6$, $R_7$ and $R_8$ are independently alkyl of 1 to 8 carbon atoms.

4. A compound according to claim 3 wherein $R_1$, $R_2$, $R_3$, $R_4$, $R_5$, $R_6$, $R_7$ and $R_8$ are independently methyl or tert-butyl.

5. A compound according to claim 1 wherein X and Y are independently a direct bond or —$CR_9R_{10}$— where $R_9$ is hydrogen, and $R_{10}$ is hydrogen, methyl or phenyl.

6. A compound according to claim 1 which is 6-{[2,4,8,10-tetra-tert-butyl-dibenzo[d,f][1,3,2]dioxaphosphepin-6-yl]oxy}-2,4,8,10-tetra-tert-butyl-dibenzo[d,f][1,3,2]dioxaphosphepin; 6-{[2,4,8,10-tetra-tert-butyl-12H-dibenzo[d,g][1,3,2]dioxaphosphocin-6-yl]oxy}-2,4,8,10-tetra-tert-butyl-12H-dibenzo[d,g][1,3,2]dioxaphosphocin; 6-{[2,4,8,10-tetra-tert-butyl-12-methyl-dibenzo[d,g][1,3,2]dioxaphosphocin-6-yl]oxy}-2,4,8,10-tetra-tert-butyl-12-methyl-dibenzo[d,g][1,3,2]dioxaphosphocin; 6-{[2,4,8,10-tetra-tert-butyl-12-methyl-dibenzo[d,g][1,3,2]dioxaphosphocin-6-yl]oxy}-2,4,8,10-tetra-tert-butyl-12-methyl-dibenzo[d,g][1,3,2]dioxaphosphocin; or 6-{[2,4,8,10-tetra-tert-butyl-dibenzo[d,f][1,3,2]dioxaphosphepin-6-yl]oxy}-2,4,8,10-tetra-tert-butyl-12H-dibenzo[d,g][1,3,2]dioxaphosphocin.

7. A composition stabilized against thermal, oxidative or light-induced degradation which comprises, (a) an organic material subject to thermal, oxidative or light-induced degradation, and (b) an effective stabilizing amount of a compound of formula I

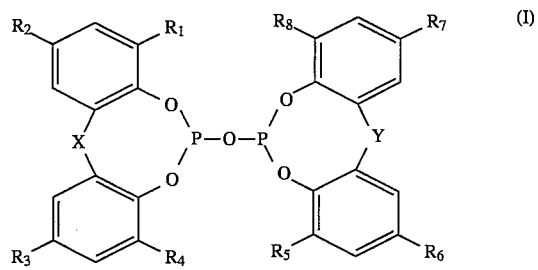

wherein $R_1$, $R_2$, $R_3$, $R_4$, $R_5$, $R_6$, $R_7$ and $R_8$ are independently hydrogen, alkyl of 1 to 18 carbon atoms, cycloalkyl of 5 to 12 carbon atoms or phenylalkyl of 7 to 15 carbon atoms, and X and Y are independently a direct bond, —S— or —$CR_9R_{10}$— where $R_9$ and $R_{10}$ are independently hydrogen or alkyl of 1 to 18 carbon atoms, or $R_{10}$ is also phenyl.

8. A composition according to claim 7 where in the compound of formula I, $R_1$, $R_2$, $R_3$, $R_4$, $R_5$, $R_6$, $R_7$ and $R_8$ are independently alkyl of 1 to 18 carbon atoms.

9. A composition according to claim 8 where in the compound of formula I, $R_1$, $R_2$, $R_3$, $R_4$, $R_5$, $R_6$, $R_7$ and $R_8$ are independently alkyl of 1 to 8 carbon atoms.

10. A composition according to claim 9 where in the compound of formula I, $R_1$, $R_2$, $R_3$, $R_4$, $R_5$, $R_6$, $R_7$ and $R_8$ are independently methyl or tert-butyl.

11. A composition according to claim 7 where in the compound of formula I, X and Y are independently a direct bond or —$CR_9R_{10}$— where $R_9$ is hydrogen, and $R_{10}$ is hydrogen, methyl or phenyl.

12. A composition according to claim 7 wherein the compound of formula I is 6-{[2,4,8,10-tetra-tert-butyl-dibenzo[d,f][1,3,2]dioxaphosphepin-6-yl]oxy}-2,4,8,10-tetra-tert-butyl-dibenzo[d,f][1,3,2]dioxaphosphepin; 6-{[2,4,8,10-tetra-tert-butyl-12H-dibenzo[d,g][1,3,2]dioxaphosphocin-6-yl]oxy}-2,4,8,10-tetra-tert-butyl-12H-dibenzo[d,g][1,3,2]dioxaphosphocin; 6-{[2,4,8,10-tetra-tert-butyl-12-methyl-dibenzo[d,g][1,3,2]dioxaphosphocin-6-yl]oxy}-2,4,8,10-tetra-tert-butyl-12-methyl-dibenzo[d,g][1,3,2]dioxaphosphocin; 6-{[2,4,8,10-tetra-tert-butyl-12-methyl-dibenzo[d,g][1,3,2]dioxaphosphocin-6-yl]oxy}-2,4,8,10-tetra-tert-butyl-12-methyl-dibenzo[d,g][1,3,2]dioxaphosphocin; or 6-{[2,4,8,10-tetra-tert-butyl-dibenzo[d,f][1,3,2]dioxaphosphepin-6-yl]oxy}-2,4,8,10-tetra-tert-butyl-12H-dibenzo[d,g][1,3,2]dioxaphosphocin.

13. A composition according to claim 7 wherein the organic material is a natural, semi-synthetic or synthetic polymer.

14. A composition according to claim 13 wherein the polymer is a thermoplastic polymer.

15. A composition according to claim 14 wherein the polymer is a polyolefin.

16. A composition according to claim 15 wherein the polyolefin is polyethylene or polypropylene.

17. A composition according to claim 16 wherein the polyolefin is polypropylene.

* * * * *